US012653803B2

(12) United States Patent
Schrauwen et al.

(10) Patent No.: US 12,653,803 B2
(45) Date of Patent: Jun. 16, 2026

(54) TREM2 AGONISTS FOR THE STIMULATION OF MICROGLIA AND METHODS OF IDENTIFICATION

(71) Applicant: THE TRANSLATIONAL GENOMICS RESEARCH INSTITUTE, Phoenix, AZ (US)

(72) Inventors: Isabelle Schrauwen, Phoenix, AZ (US); Matthew Huentelman, Phoenix, AZ (US); Wayne Jepsen, Tempe, AZ (US)

(73) Assignee: THE TRANSLATIONAL GENOMICS RESEARCH INSTITUTE, Phoenix, AZ (US)

( * ) Notice: Subject to any disclaimer, the term of this patent is extended or adjusted under 35 U.S.C. 154(b) by 159 days.

(21) Appl. No.: 16/757,299

(22) PCT Filed: Oct. 17, 2018

(86) PCT No.: PCT/US2018/056392
§ 371 (c)(1),
(2) Date: Apr. 17, 2020

(87) PCT Pub. No.: WO2019/079529
PCT Pub. Date: Apr. 25, 2019

(65) Prior Publication Data
US 2021/0186917 A1      Jun. 24, 2021

Related U.S. Application Data

(60) Provisional application No. 62/573,400, filed on Oct. 17, 2017.

(51) Int. Cl.
*A61K 31/277* (2006.01)
*A61K 31/421* (2006.01)
*G01N 33/50* (2006.01)

(52) U.S. Cl.
CPC .......... *A61K 31/277* (2013.01); *A61K 31/421* (2013.01); *G01N 33/5023* (2013.01)

(58) Field of Classification Search
CPC . A61K 31/277; A61K 31/421; G01N 33/5023
See application file for complete search history.

(56) References Cited

U.S. PATENT DOCUMENTS

2017/0274075 A1      9/2017  Rahimi

FOREIGN PATENT DOCUMENTS

WO      WO-2005016333 A1 *  2/2005    ........... A61K 31/275
WO      WO-2011133668 A2 *  10/2011   ......... A61K 31/4741
WO         2017/058866 A1     4/2017

OTHER PUBLICATIONS

Hart et al. Phagocytosis of apoptotic cells Methods vol. 44, Issue 3, Mar. 2008, pp. 280-285 (Year: 2008).*

Mucke and Selkoe (Cold Spring Harb Perspect Med. Jul. 2012; 2(7)) (Year: 2012).*
Jonsson et al. N Engl J Med 2013; 368:107-116. (Year: 2013).*
Davis et al. PLoS One vol. 8 Issue: 1 pp. e54127 Jan. 2013 (Year: 2013).*
Difference between pharmacokinetics and pharmacological— Google Search Sep. 2024 Accessed Sep. 23, 2024 (Year: 2024).*
Sasaki et al., "Microglia and brain macrophages: an update", Neuropathology, 37(5):452-464 (Oct. 2016).
Giraldo, M., et al. Variants in triggering receptor expressed on myeloid cells 2 are associated with both behavioral variant frontotemporal lobar degeneration and Alzheimer's disease. Neurobiol Aging 2013; 34(8):2077.e11-8.
Strobel, S., et al. Changes in the expression of genes related to neuroinflammation over the course of sporadic Alzheimer's disease progression: CX3CL1, TREM2, and PPARγ. J Neural Transm 2015; 122(7):1069-1076.
Hu, N., et al. Increased expression of TREM2 in peripheral blood of Alzheimer's disease patients. J Alzheimers Dis 2014; 38(3):497-501.
Sanderson, S, et al. LacZ inducible, antigen/MHC-specific T cell hybrids. Int Immunol 1994; 6(3):369-376.
Coleman, J. E., et al. Efficient large-scale production and concentration of HIV-1-based lentiviral vectors for use in vivo. Physiol Genomics 2003; 12(3):221-228.
Daws, M. R., et al. Pattern recognition by TREM-2: binding of anionic ligands. J Immunol 2003; 171(2):594-599.
Boss, V., et al. Induction of NFAT-mediated transcription by Gq-coupled receptors in lymphoid and non-lymphoid cells. J Biol Chem 1996; 271(18):10429-10432.
Wang, Y., et al. TREM2 lipid sensing sustains the microglial response in an Alzheimer's disease model. Cell 2015;160(6):1061-1071.
Golde, T.E., et al. Alzheimer's disease risk alleles in TREM2 illuminate innate immunity in Alzheimer's disease. Alzheimers Res Ther 2013; 5(3):24.
Choi, S.H., et al. A three-dimensional human neural cell culture model of Alzheimer's disease. Nature 2014; 515(7526):274-278.
Jiang, T. et al. Upregulation of TREM2 ameliorates neuropathology and rescues spatial cognitive impairment in a transgenic mouse model of Alzheimer's disease. Neuropsychopharmacology 2014; 39(13):2949-2962.
Lawson, L.J., et al. Turnover of resident microglia in the normal adult mouse brain. Neuroscience 1992; 48:405-415.

(Continued)

*Primary Examiner* — Adam C Milligan
*Assistant Examiner* — William Y Lee
(74) *Attorney, Agent, or Firm* — FULLER IP LAW; Rodney J. Fuller

(57) ABSTRACT

The present disclosure is directed to methods of promoting phagocytosis, particularly the phagocytic activity of microglia via activation of triggering receptor expressed on myeloid cells 2 (TREM2). The present disclosure is also directed to methods of activating TREM2 in a cell, particularly a neuronal cell exhibiting an accumulation of a pathogenic protein. The present disclosure is directed to detecting an effect of a compound on the TREM2 activity as well.

9 Claims, 7 Drawing Sheets

(56) References Cited

OTHER PUBLICATIONS

Carro, E. et. al. Blockade of the insulin-like growth factor I receptor in the choroid plexus originates Alzheimer's-like neuropathology in rodents: New cues into the human disease? Neurobiology of Aging 27, 2006.1618-1631.

Galloway, D. A., Phillips, A. E., Owen, D. R., & Moore, C. S. (2019). Phagocytosis in the brain: homeostasis and disease. Frontiers in immunology, 10, 790.

Longwood Screening Facility LOPAC1 Dec. 28, 2023.

Martin, Y. C., Kofron, J. L., & Traphagen, L. M. (2002). Do structurally similar molecules have similar biological activity?. Journal of medicinal chemistry, 45(19), 4350-4358.

Torres-Aleman, I. Mouse Models of Alzheimer's Dementia: Current Concepts and New Trends. Endocrinology, Dec. 2008. 14(12): 5952-5957.

Westwood, A. J. et. al. Insulin-Like Growth Factor-1 and Risk of Alzheimer Dementia and Brain Atrophy. American Academy of Neurology. Neurology 82. May 6, 2014. 1613-1619.

* cited by examiner

TREM2 AGONISTS FOR THE STIMULATION OF MICROGLIA AND METHODS OF IDENTIFICATION

CROSS-REFERENCE TO RELATED APPLICATIONS

This application is the U.S. National Stage of International Application No. PCT/US2018/056392, filed on Oct. 17, 2018, which claims the benefit of U.S. Provisional Patent Application No. 62/573,400, filed on Oct. 17, 2017, the contents of each of which are incorporated herein by reference in their entireties.

STATEMENT REGARDING FEDERALLY SPONSORED RESEARCH OR DEVELOPMENT

This invention was made with governmental support under grant number AG019610 awarded by the National Institutes of Health (NIH). The United States government has certain rights in the invention.

TECHNICAL FIELD

The present disclosure relates to methods of using stimulate triggering receptor expressed on myeloid cells 2 (TREM2) agonists in treating neurodegenerative and other TREM2-associated diseases. The present disclosure also relates to methods of detecting an effect of a compound on TREM2 activity, including identifying TREM2 agonists.

BACKGROUND OF THE INVENTION

The global prevalence of dementia is projected to increase in the coming decades as the population ages. Alzheimer's disease (AD) is a leading cause of dementia, and current FDA-approved drugs for AD do not prevent or reverse the disease and provide only modest symptomatic benefits. Alterations in both astrocytes and microglia, reflecting underlying changes in innate immune activation within the brain, are invariant pathological features of neurodegenerative disorders such as Alzheimer's disease. Thus, there is a need to identify new therapeutic avenues for Alzheimer's disease and other neurodegenerative disorders.

Several studies have demonstrated that genetic variants in triggering receptor expressed on myeloid cells 2 (TREM2), a known regulator of microglial activation and phagocytosis, confer substantial risk to several forms of dementia and neurodegenerative disease. TREM2 has been shown to recognize lipopolysaccharides in the cell wall of bacteria and triggers the phagocytic uptake of bacteria. In the nervous system, TREM2 has been shown to play a critical role in the engulfment of apoptotic neuronal cells by microglia and the resolution of neuroinflammation. Following neuronal injury, microglia initiate repair by phagocytizing dead neurons without eliciting inflammation, and TREM2 has been shown to play a role in the phagocytosis of apoptotic neuronal cells by microglia and resolution of inflammation. TREM2 can directly bind to neuronal cells, with increased binding to apoptotic neuronal cells. When neuronal cells undergo apoptosis, they increase the expression of TREM2-ligands, which mediate signal transduction by TREM2 on microglia and promote phagocytosis. Transmembrane signaling via TREM2 is accomplished through an immunoreceptor tyrosine-based activation motif (ITAM) bearing transmembrane adaptor protein, TYRO protein tyrosine kinase binding protein (TYROBP, also known as DAP12).

TREM2 is highly expressed in brain regions with pronounced vulnerability to AD-related changes, such as the hippocampus. Most dementias are characterized by neuronal loss and accumulation of insoluble protein aggregates. Recessive mutations in TREM2 cause Polycystic lipomembranous osteodysplasia with sclerosing leukoencephalopathy (PLOSL), pure early-onset dementia, frontotemporal dementia (FTD)-like syndrome and behavioral variant FTLD. Also, a TREM2 variant p.Arg47His (or "R47H") is associated with an increased risk of Alzheimer's disease, and heterozygote carriers of p.Gln33X (PLOSL and FTD-like) were reported to show memory deficits. Lastly, other studies have implicated TREM2 in experimental autoimmune encephalomyelitis, an animal model for multiple sclerosis (MS), Parkinson's disease (PD), and amyotrophic lateral sclerosis (ALS) as well. Mutations in TREM2 that cause PLOSL and bvFTLD lead to a less functional or a complete loss of function version of TREM2.

Although the exact pathophysiology why the loss-of-function mutation in TREM2 causes a neurodegenerative phenotype is unknown, the TREM2 function may affect AD pathology by impairing the clearance of amyloid and apoptotic neurons by microglia, which leads to the accumulation of multiple types of extracellular debris in the brain. This accumulation further compounds the cascade of neuroinflammation, and additional debris deposition in a cyclic fashion that eventually participates in the cell death noted in Alzheimer's disease patients. Recent in vitro and in vivo TREM2 overexpression studies support this hypothesis. Overexpressing TREM2 in APPswe/PS1dE9 transgenic mice showed a decreased accumulation of amyloid plaques, neuroinflammation, loss of neurons and synapses, and increased spatial memory, compared to non-transfected transgenic mice. TREM2 overexpression also facilitated Aβ1-42 phagocytosis in cultured primary microglia. In addition to Aβ clearance, TREM2 could also be important in other processes such as regulation of cell-to-cell transmission of tau and the induction of other intracellular proteinopathies.

Under the assumption that the TREM2 low-frequency polymorphism (p.Arg47His) does not function as a dominant negative molecule, this may represent a therapeutic avenue for treatment or prevention of the neurodegenerative disease in the p.Arg47His heterozygotes and AD in general. It is also important to note that the rarity of the p.Arg47His variant results in most carriers existing in the heterozygous state in the general population. This is important, as they likely express a wild-type version of TREM2 in addition to the mutant version.

Thus, a TREM2 activity likely can be stimulated in the AD brain (especially during the early stages of the disease before dementia onset), to enhance amyloid clearance and quiet neuroinflammatory processes. As such, exploring agonists of TREM2 may be important in dementia and memory. In addition to p.Arg47His carriers and other TREM2-related dementias, TREM2 agonists may also be important for normal memory function and in the prevention or treatment of Alzheimer's Disease in general. Accordingly, agonists of TREM2 must be identified.

SUMMARY OF THE INVENTION

The present disclosure provides useful methods for treating a subject who is in need of promoting phagocytosis of an apoptotic cell, including administering to the subject a sufficient amount of a compound selected from Tyrphostin AG 538, AC1NS458, IN1040, Butein, Okanin, AGL 2263, GB19, GB16, GB20, GB17, GB18, GB21, GB22, GB27, GB44, GB42, GB2, 4,4'-Dihydroxychalcone, 3,4-Dihydroxybenzophenone, and derivatives or salts thereof, to promote phagocytosis of the apoptotic cell in the subject. In certain aspects, the compound is Tyrphostin AG 538 or salts thereof.

In some embodiments, the subject is an animal model of or a human having or diagnosed with a neurodegenerative disease. In an exemplary embodiment, the apoptotic cell of the subject is a neuronal cell exhibiting an accumulation of a pathogenic protein such as huntingtin with polyglutamine expansion, atrophin-1, ataxin-1, ataxin-2, ataxin-3, AP peptide (APP), hyperphosphorylated tau protein, α-Synuclein, Parkin, or Prion protein. In another exemplary embodiment, the neurodegenerative disease is Alzheimer's disease (AD), Amyotrophic lateral sclerosis (ALS), Huntington's disease (HD), Parkinson's disease (PD), chronic traumatic encephalopathy, Dentatorubral-pallidoluysian atrophy (DRPLA), Spinocerebellar ataxia (SCA), Traumatic brain injury (TBI), Stroke, Paraneoplastic disorders, Systemic lupus erythematous, Multiple sclerosis (MS), or a Prion disease. The Prion disease may be Creutzfeldt-Jakob disease (CJD), new variant CJD, Gerstmann-Sträussler-Scheinker syndrome (GSS), fatal familial insomnia (FFI), or kuru.

In some aspects, the subject is an animal model or a human having or diagnosed with a disease associated with TREM2, such as a disease caused by a mutation in TREM2, of which a TREM2 variant has been identified as a risk factor, the outcome of which is affected by TREM2 deficiency, or of which TREM2 is a potential therapeutical target. In an exemplary embodiment, the disease associated with TREM2 is Nasu Hakola disease (NHD or PLOSL), frontotemporal dementia (FTD), Autoimmune Lymphoproliferative Syndrome (ALPS), Multiple sclerosis (MS), Amyotrophic lateral sclerosis (ALS), autoimmune encephalitis (AE), prion disease, stroke, pain, medial cerebral artery occlusion (MCAO), or traumatic brain injury (TBI).

In further embodiments, the subject is selected based on a cognitive decline, a family history of a neurodegenerative disease, having and/or diagnosed with a neurodegenerative or TREM2-associated disease with an immune neuroinflammatory component, or combinations thereof. The cognitive decline in the subject may be very mild, mild, or moderate.

The present disclosure also provides useful methods for activating triggering receptor expressed on myeloid cells 2 (TREM2) in a cell, including contacting the cell with a sufficient amount of a compound selected from Tyrphostin AG 538, AC1NS458, IN1040, Butein, Okanin, AGL 2263, GB19, GB16, GB20, GB17, GB18, GB21, GB22, GB27, GB44, GB42, GB2, 4,4'-Dihydroxychalcone, 3,4-Dihydroxybenzophenone, and derivatives or salts thereof, to activate TREM2 in the cell.

In some embodiments, the cell is a mononuclear phagocyte, a dendritic cell, a granulocyte, a bone marrow-derived macrophage, a monocyte-derived macrophage, a tissue macrophage, a Kuppfer cell, an alveolar macrophage, an osteoclast, or a circulating monocyte. In other embodiments, the mononuclear phagocyte is microglia, osteoclast, or alveolar macrophage. In some aspects, the tissue macrophage is splenocyte. In further embodiments, the cell is selected based on TREM2 upregulation in the central nervous system (CNS) including the hippocampus, hypothalamus, cerebral cortex, caudate, and/or cerebellum. In an exemplary embodiment, the cell is microglia.

The present disclosure further provides useful methods for detecting an effect of a compound on the triggering receptor expressed on myeloid cells 2 (TREM2) activity, including the steps of: applying the compound to a host cell expressing TREM2, TYROBP, and a synthetic sequence comprising an NFAT-response element and a nucleotide sequence encoding a reporter; and measuring a signal emitted by the reporter in the host cell. In an exemplary embodiment, the reporter includes firefly luciferase.

In some embodiments, the signal is compared to a signal in negative control. In some aspects, the negative control is a host-cell equivalent, except for expressing an undetectable amount of TREM2 and/or TYROBP. For example, less than 20 fg of TREM2 and/or TYROBP protein per cell. In other aspects, the negative control is a host-cell equivalent, except for expressing a fraction amount, for example, less than 5%, of TREM2 and/or TYROBP protein on the membrane compared to the host cell. In an exemplary embodiment, the compound is selected as a TREM2 agonist if the signal produced in the host cell is at least 5-fold higher than the signal in the negative control cell.

In some embodiments, the signal is compared to a signal in positive control. In some aspects, the positive control is a host-cell equivalent, and an agonist of the TREM2 signaling pathway is applied to the positive control. In an exemplary embodiment, the agonist includes phorbol myristate acetate (PMA) and a $Ca^{2+}$ ionophore. In another exemplary embodiment, the agonist includes sphingomyelin. In some aspects, the compound is selected as a TREM2 agonist if the signal produced in the host cell is at least 50% of the signal in the positive control. In a particular aspect, the method includes plating the host cell, the negative control cell, and/or the positive control cell in a 384-well plate.

BRIEF DESCRIPTION OF THE DRAWINGS

FIG. 2A TREM2 forms a membrane receptor complex with TYROBP. FIG. 2B Upon stimulation of TREM2/TYROBP, a firefly luciferase reporter is activated through NFAT-response elements, leading to increases in luminescence when luciferin is added.

FIG. 4A RT-PCR results from total RNA extracted from TREM2/TYROBP/NFAT-Luc (NFAT+TR2/TYR), NFAT-Luc (NFAT), BW5147.3 (BW) control cells, or a no-template control (BL). Only TREM2/TYROBP/NFAT-Luc (NFAT+TR2/TYR) cells expressed TREM2 and TYROBP. Beta-2 microglobulin (B2M) was used as a positive control. FIG. 4B Wild-type (WT) TREM2 is not expressed in BW5147.3 control cells. TR2/TYR stable cells express a codon-optimized version of TREM2 and TYROBP. FIG. 4C Relative luminescence after NFAT-Luc (NFAT) or BW5147.3 (BW) cells were stimulated by Ionomycin and PMA, synergetic NFAT stimulators. NFAT-Luc shows a significant increase in luminescence. RLU: relative luminescence units. FIG. 4D Relative luminescence after TREM2/TYROBP/NFAT-Luc (NFAT+TR2/TYR) or NFAT-Luc (NFAT) cells were stimulated by Ionomycin and PMA, synergetic NFAT stimulators.

FIG. 6A A primary screen using 5 μM Tyrphostin AG 538 (in duplicates) with the TREM2/TYROBP/NFAT-Luc reporter cell line (NFAT+TR2/TYR), which identified Tyrphostin AG 538 as a positive hit (relative luminescence=16.08). Sphingomyelin (120 μg/mL), a known TREM2 agonist, was used as a positive control. FIG. 6B A counter screen with the NFAT-Luc reporter cell line (NFAT). Various concentrations of Tyrphostin AG 538 (1.5, 3, 6, and 12.5 μM) did not stimulate the NFAT reporter directly. PMA (1.5 ng/μl)/ Ionomycin (0.375 μM), a known NFAT reporter stimulant, was used as a positive control in both experiments.

DETAILED DESCRIPTION OF THE INVENTION

Figure 1:
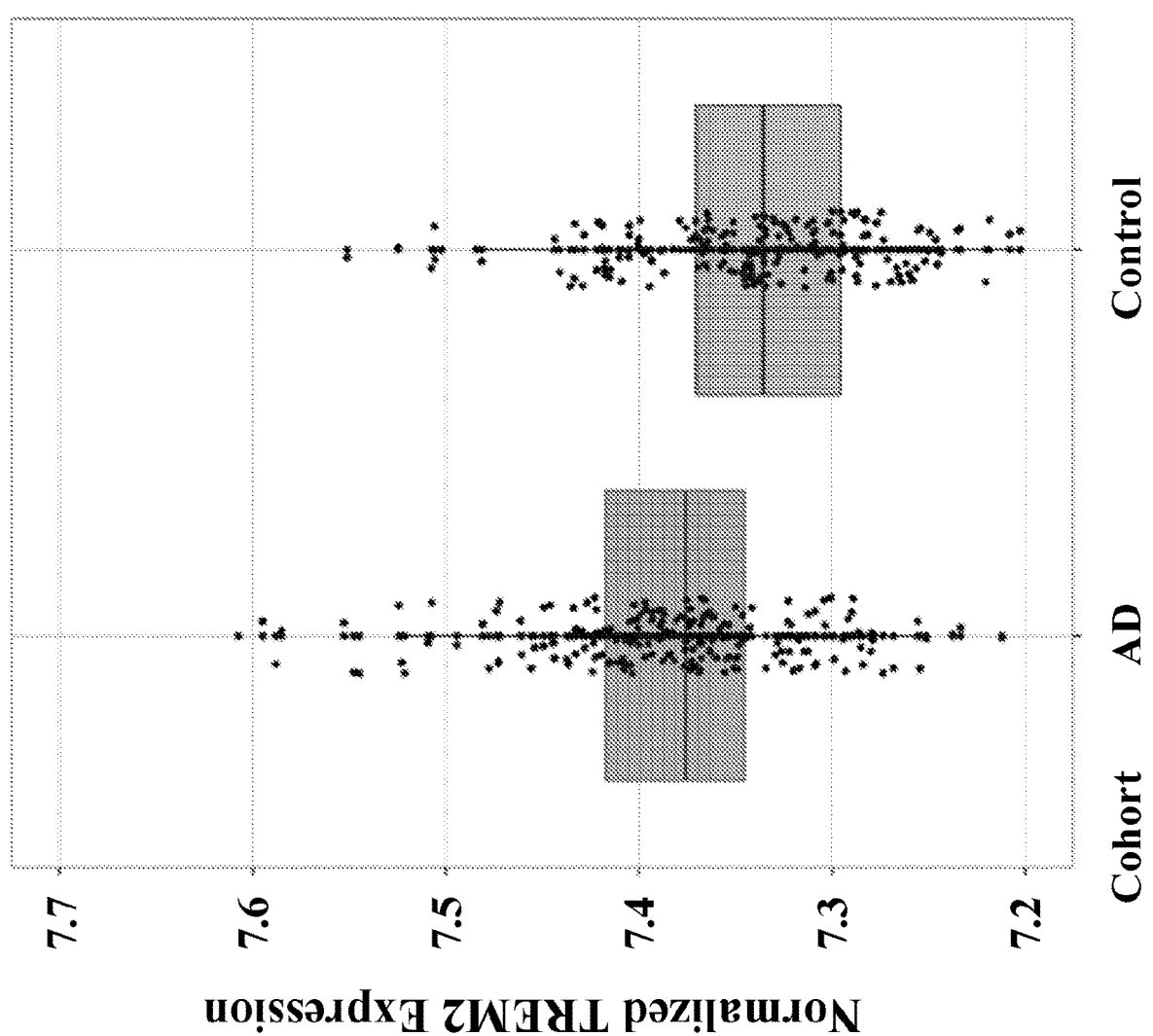
FIG. 1 depicts TREM2 expression in the frontal and temporal region of the brains of control subjects and subjects with Alzheimer's disease (AD). The TREM2 expression is increased in AD brain.

Herein the inventors disclose a method of treating a subject in need of promoting phagocytosis of an apoptotic cell. Typically, the method comprises administering to the subject a compound selected from the group consisting of: Tyrphostin AG 538, AC1NS458, IN1040, Butein, Okanin, AGL 2263, GB19, GB16, GB20, GB17, GB18, GB21, GB22, GB27, GB44, GB42, GB2, 4,4'-Dihydroxychalcone, 3,4-Dihydroxybenzophenone, derivatives thereof, and salts thereof, in an amount sufficient to promote phagocytosis of the apoptotic cell in the subject.

In some embodiments, the compound comprises Tyrphostin AG 538, derivative(s) thereof, or salt(s) thereof. In other embodiments, the compound comprises Tyrphostin AG 538 or salt(s) thereof.

In yet other embodiments, the subject is an animal. In preferred embodiments, the subject is a mammal, for example, a mouse, a rat, a cat, a dog, a pig, a monkey, or a human, etc.

In some aspects, the mammal is an animal model of a neurodegenerative disease. In other aspects, the subject is a human having and/or diagnosed with a neurodegenerative disease. In yet other aspects, the neurodegenerative disease is associated with an accumulation of a pathogenic protein. Non-limiting examples of neurodegenerative diseases associated with an accumulation of a pathogenic protein include Alzheimer's disease (AD), Amyotrophic lateral sclerosis (ALS), Huntington's disease (HD), Parkinson's disease (PD), chronic traumatic encephalopathy, Dentatorubral-pallidoluysian atrophy (DRPLA), Spinocerebellar ataxia (SCA), and a Prion disease, etc. Non-limiting examples of Prion diseases include Creutzfeldt-Jakob disease (CJD), new variant CJD, Gerstmann-Sträussler-Scheinker syndrome (GSS), fatal familial insomnia (FFI), and kuru, etc.

In further aspects, the mammal is an animal model of a disease associated with TREM2. In yet further aspects, the mammal is a human having and/or diagnosed with a disease associated with TREM2. Non-limiting examples of the TREM2-associated diseases include a disease caused by a mutation in TREM2, a disease of which a TREM2 variant has been identified as a risk factor, a disease the outcome of which is affected by TREM2 deficiency, and a disease of which TREM2 is a potential therapeutical target, etc. Non-limiting, specific examples of the TREM2-associated diseases include Nasu Hakola disease (NHD or PLOSL), frontotemporal dementia (FTD), Autoimmune Lymphoproliferative Syndrome (ALPS), Multiple sclerosis (MS), Amyotrophic lateral sclerosis (ALS), autoimmune encephalitis (AE), prion disease, stroke, pain, medial cerebral artery occlusion (MCAO), and traumatic brain injury (TBI), etc.

In some aspects, the neurodegenerative disease or the TREM2-associated disease has an immune neuroinflammatory component or a suspected immune neuroinflammatory component. As used herein, the term "an immune neuroinflammatory component" refers to a pathology that includes inflammation of the nervous tissue. Non-limiting examples of the neurodegenerative disease with an immune neuroinflammatory component include AD, PD, neurotropic viral infections, stroke, paraneoplastic disorders, TBI, ischemic brain injury, Systemic lupus erythematous, and MS, etc. In particular aspects, inflammation of the nervous tissue includes, for example, chronic inflammation caused by sustained activation of glial cells, recruitment of immune cells into the brain, or both. Non-limiting examples of triggers of chronic inflammation include toxic metabolites, autoimmunity, aging, microbes, viruses, traumatic brain injury, air pollution, and passive smoking, etc.

In specific embodiments of the disclosure, the subject has an amyloid accumulation in the brain. For example, a patient with dementia, AD, or diagnosed with stage 4 moderate cognitive decline, etc. In other specific embodiments of the disclosure, the subject has an accumulation of beta-amyloid, tau protein, or both in the brain. For example, a patient diagnosed with stage 2 very mild cognitive decline, diagnosed with stage 3 mild cognitive decline, or without cognitive decline but has a family history of a neurodegenerative disease such as dementia and AD. In some aspects, the subject has a neurodegenerative disease with an immune neuroinflammatory component or with a suspected neuroinflammatory component, e.g., AD, frontotemporal dementia, chronic traumatic encephalopathy, or Down's syndrome. Some embodiments of the methods further comprise selecting the subject based on a family history of a neurodegenerative disease, a cognitive decline, or both. The extent of the cognitive decline includes very severe, severe, moderate, mild, and very mild, etc. Other embodiments of the methods further comprise selecting the subject based on a need for increasing microglial activity, e.g., the phagocytic activity of microglia. In some aspects, the Global Deterioration Scale (GDS) is used. In other aspects, the Reisberg Scale is used.

In some aspects, the apoptotic cell is a neuronal cell. In other aspects, the apoptotic cell exhibits an accumulation of a pathogenic protein. Non-limiting examples of the pathogenic protein include huntingtin with polyglutamine expansion, atrophin-1, ataxin-1, ataxin-2, ataxin-3, Aβ peptide (APP), hyperphosphorylated tau protein, α-Synuclein, Parkin, and Prion protein, etc.

Herein the inventors also disclose a method of activating triggering receptor expressed on myeloid cells 2 (TREM2) in a cell. Typically, the method comprises contacting the cell with a compound selected from the group consisting of: Tyrphostin AG 538, AC1NS458, IN1040, Butein, Okanin, AGL 2263, GB19, GB16, GB20, GB17, GB18, GB21, GB22, GB27, GB44, GB42, GB2, 4,4'-Dihydroxychalcone, 3,4-Dihydroxybenzophenone, derivatives thereof, and salts thereof, in an amount sufficient to activate TREM2 in the cell.

In some embodiments, the compound comprises Tyrphostin AG 538, derivative(s) thereof, or salt(s) thereof. In other embodiments, the compound comprises Tyrphostin AG 538 or salt(s) thereof.

In other embodiments, the cell is selected from the group consisting of: a mononuclear phagocyte, a dendritic cell, a granulocyte, a bone marrow-derived macrophage, a monocyte-derived macrophage, a tissue macrophage, a Kuppfer cell, an alveolar macrophage, an osteoclast, and a circulating monocyte. Non-limiting examples of the mononuclear phagocyte include microglia, osteoclast, and alveolar macrophage, etc. In some aspects, the tissue macrophage is splenocyte. In some embodiments, the cell is microglia in the central nervous system (CNS), for example, the hippocampus, hypothalamus, cerebral cortex, caudate, and cerebellum, etc.

In some aspects, the methods further comprise selecting the cell based on TREM2 upregulation.

Herein the inventors also disclose a method for detecting an effect of a compound on triggering receptor expressed on myeloid cells 2 (TREM2) activity. Typically, the method comprises applying the compound to the host cell and measuring a signal emitted by the reporter in the host cell. In preferred embodiments, the host cell expresses TREM2 and TYRO protein tyrosine kinase binding protein (TYROBP), and the host cell has a synthetic sequence comprising an NFAT-response element and a nucleotide sequence encoding a reporter.

Non-limiting examples of the reporters include firefly luciferase, chloramphenicol acetyltransferase (CAT), β-galactosidase (LacZ), blue/UV protein, cyan protein, green fluorescent protein (GFP), yellow protein, orange protein, red fluorescent protein (RFP), far-red protein, near-IR protein, long stokes shift protein, photoactivatable protein, photoconvertible protein, and photoswitchable protein, etc.

Non-limiting examples of the blue protein include TagBFP, mTagBFP2, Azurite, EBFP2, mKalamal, Sirius, Sapphire, and T-Sapphire, etc. Non-limiting examples of the cyan protein include ECFP, Cerulean, SCFP3A, mTurquoise, mTurquoise2, monomeric Midoriishi-Cyan, TagCFP, and mTFP1, etc. Non-limiting examples of the green protein include EGFP, Emerald, Superfolder GFP, Monomeric Azami Green, TagGFP2, mUKG, mWasabi, Clover, and mNeonGreen, etc. Non-limiting examples of the yellow protein include EYFP, Citrine, Venus, SYFP2, and TagYFP, etc.

Non-limiting examples of the orange protein include Monomeric Kusabira-Orange, mKOK, mKO2, mOrange, and mOrange2, etc. Non-limiting examples of the red protein include mRaspberry, mCherry, mStrawberry, mTangerine, tdTomato, TagRFP, TagRFP-T, mApple, mRuby, and mRuby2, etc. Non-limiting examples of the far red protein include mPlum, HcRed-Tandem, mKate2, mNeptune, and NirFP, etc.

Non-limiting examples of the Near-IR Protein include TagRFP657, IFP1.4, and iRFP, etc. Non-limiting examples of the Long Stokes Shift Protein include mKeima Red, LSS-mKate1, LSS-mKate2, and mBeRFP, etc. Non-limiting examples of the Photoactivatable Protein include PA-GFP, PAmCherryl, and PATagRFP, etc.

Non-limiting examples of the Photoconvertible Protein include Kaede (green), Kaede (red), KikGR1 (green), KikGR1 (red), PS-CFP2 (400 $\lambda_{ex}$), PS-CFP2 (490 $\lambda_{ex}$), mEos2 (green), mEos2 (red), mEos3.2 (green), mEos3.2 (red), PSmOrange (548 $\lambda_{ex}$), and PSmOrange (634 $\lambda_{ex}$), etc. Non-limiting examples of the Photoswitchable Protein include Dronpa, etc.

In some aspects, the reporter comprises firefly luciferase.

In other aspects, the methods further comprise deriving an EC50 value (half maximal effective concentration) of the compound in the host cell. A person skilled in the art would know how to derive EC50 of the compound for the reporter activity. In some embodiments, the EC50 is derived by fitting the following equation:

$$Y = \min + (\max - \min) / \left( 1 + \left( \frac{X}{EC50} \right)^{-Hill\ coefficient} \right)$$

X is the concentration of the compound, Y is the intensity or ratio of the reporter signal, and Max and min are the top and the bottom of the reporter intensity or ratio versus concentration curve, respectively.

In some embodiments, the methods further comprise measuring a signal emitted in a negative control. Non-limiting examples of the negative control include a blank (e.g., no cell, no substrate, or both), the host cell before application of the compound, a cell that is not exposed to the compound, a cell that does not express the reporter, a cell that expresses an undetectable amount of TREM2, TYROBP, or both, and a cell that expresses a fraction of TREM2 and/or TYROBP protein compared to the host cell, etc. In some aspects, the methods further comprise applying the compound to the negative control cell.

As used herein, "an undetectable amount" refers to an amount of TREM2 or TYROBP protein that is less than the lowest level of sensitivity of whatever assay is used in practicing the claimed methods. For example, if Western blotting is used, "an undetectable amount" refers to less than 20 fg, less than 10 fg, less than 5 fg, less than 2 fg, or less than 1 fg TREM2 or TYROBP protein per cell.

In some aspects, the expression level of TREM2 protein in the negative control cell is 0-30% of the expression level of TREM2 protein in the host cell, or any percent range in between, e.g., 0.01-30%, 0.01-25%, 0.02-25%, 0.02-20%, 0.04-20%, 0.04-15%, 0.1-15%, 0.1-10%, 0.2-10%, 0.2-5%, 0.5-5%, 0.5-2.5%, 1-2.5%, and 1-2%, etc. In other aspects, the expression level of TYROBP protein in the negative control cell is 0-30% of the expression level of TYROBP protein in the host cell, or any percent range in between, e.g., 0.01-30%, 0.01-25%, 0.02-25%, 0.02-20%, 0.04-20%, 0.04-15%, 0.1-15%, 0.1-10%, 0.2-10%, 0.2-5%, 0.5-5%, 0.5-2.5%, 1-2.5%, and 1-2%, etc.

In yet other aspects, the expression level of TREM2 protein in the negative control cell is less than 10%, less than 5%, less than 2%, less than 1%, less than 0.3%, less than 0.1%, less than 0.03%, less than 0.01%, less than 0.003%, or less than 0.001% of the expression level of TREM2 protein in the host cell. In further aspects, the expression level of TYROBP in the negative control cell is less than 10%, less than 5%, less than 2%, less than 1%, less than 0.3%, less than 0.1%, less than 0.03%, less than 0.01%, less than 0.003%, or less than 0.001% of the expression level of TYROBP protein in the host cell.

In some embodiments, the methods further comprise comparing the signal emitted by the reporter in the host cell with the signal emitted in the negative control. In other embodiments, the compound is selected as a TREM2 agonist if the signal emitted in the host cell is higher than the signal emitted in the negative control by at least 50%, at least 100%, at least 2 fold, at least 5 fold, at least 10 fold, at least 20 fold, or at least 50 fold. In yet other embodiments, the compound is selected as a TREM2 agonist if the signal emitted in the host cell is between 1.5-100 fold of the signal emitted in the negative control, or any number range in between, e.g., 1.5-90 fold, 2-90 fold, 2-80 fold, 3-80 fold, 3-60 fold, 4-60 fold, 4-50 fold, 5-50 fold, 5-40 fold, 10-40 fold, 10-30 fold, 15-30 fold, and 15-20 fold, etc.

In some aspects, the methods further comprise measuring a signal emitted in a positive control. In other aspects, the positive control is a cell having the synthetic sequence comprising the NFAT-response element and the nucleotide sequence encoding the reporter. In yet other aspects, the methods further comprise applying phorbol myristate acetate (PMA) and a $Ca^{2+}$ ionophore to the positive control cell. A non-limiting example of $Ca^{2+}$ ionophore is ionomy-cin. In further aspects, the methods further comprise applying a known agonist of the TREM-2 pathway to the positive control cell. A non-limiting example of the agonist of the TREM-2 pathway is sphingomyelin.

In some embodiments, the methods further comprising selecting the compound as a TREM2 agonist if the signal produced by the compound in the host cell is at least 50% of the signal in the positive control cell.

In some aspects, the positive control cell is the host cell.

In some embodiments, the method is a high-throughput screening (HTS) assay. Some embodiments of the HTS assay further comprises a quality control (QC) step. Non-limiting examples of the QC steps include an easily mea-surable signal, a signal-to-noise ratio (maximal signal vs. background signal), an across-plate coefficient-of-variation, and a measure of statistical effect size (e.g., Z-factor) (Z-factor was calculated (0.64)), etc. In some aspects, the emission data is accepted if the signal-to-noise ratio is greater than 5. In other aspects, the emission data is accepted if the across-plate coefficient-of-variation is less than 10%. In yet other aspects, the emission data is accepted if Z-factor is greater than 0.5.

As used herein, the verb "comprise" and its conjugations are used in its non-limiting sense to mean that items fol-lowing the word are included, but items not specifically mentioned are not excluded. Also, reference to an element by the indefinite article "a" or "an" does not exclude the possibility that more than one of the elements are present unless the context clearly requires that there is one and only one of the elements. The indefinite article "a" or "an" thus usually means "at least one."

EXAMPLES

It should be understood that while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

Example 1. Upregulation of TREM2 in AD Brain

TREM2 function may affect AD pathology through the phagocytosis of amyloid plaque deposits and other debris, and recent studies overexpressing TREM2 in vitro and in vivo support this hypothesis. Replicative evidence for the association of R47H with AD and show that TREM2 is upregulated in brain tissue from patients (FIG. 1). This upregulation has been confirmed by several other subse-quent studies involving brain and peripheral blood as well. This upregulation might be stimulated by the surrounding dying neurons in the AD.

Thus, agonists of TREM2 could increase the clearance of amyloid-β, apoptotic neurons, and other debris in the brain and may, therefore, act to prevent or to slow disease progression when administered during the optimal timeframe. Specifically, stimulated TREM2 activity in the AD brain (especially during the early stages of the disease before dementia onset) is expected to enhance amyloid clearance and quiet neuroinflammatory processes. This hypothesis is strengthened by studies overexpressing TREM2 in APPswe/PS1dE9 transgenic mice, which resulted in decreased accu-mulation of amyloid plaques, neuroinflammation, and loss of neurons and synapses, and increased spatial memory compared to non-transfected transgenic mice. TREM2 over-expression also increased facilitated Aβ1-42 phagocytosis in cultured primary microglia. In addition to Aβ clearance, TREM2 could also be important in other processes such as regulation of cell-to-cell transmission of tau and the induc-tion of other intracellular proteinopathies. Overall, efficient targeting of the TREM2/TYROBP signaling pathway is expected to have application for improved clinical manage-ment across a broad range of neurodegenerative disorders.

Figures 2A, 2B:
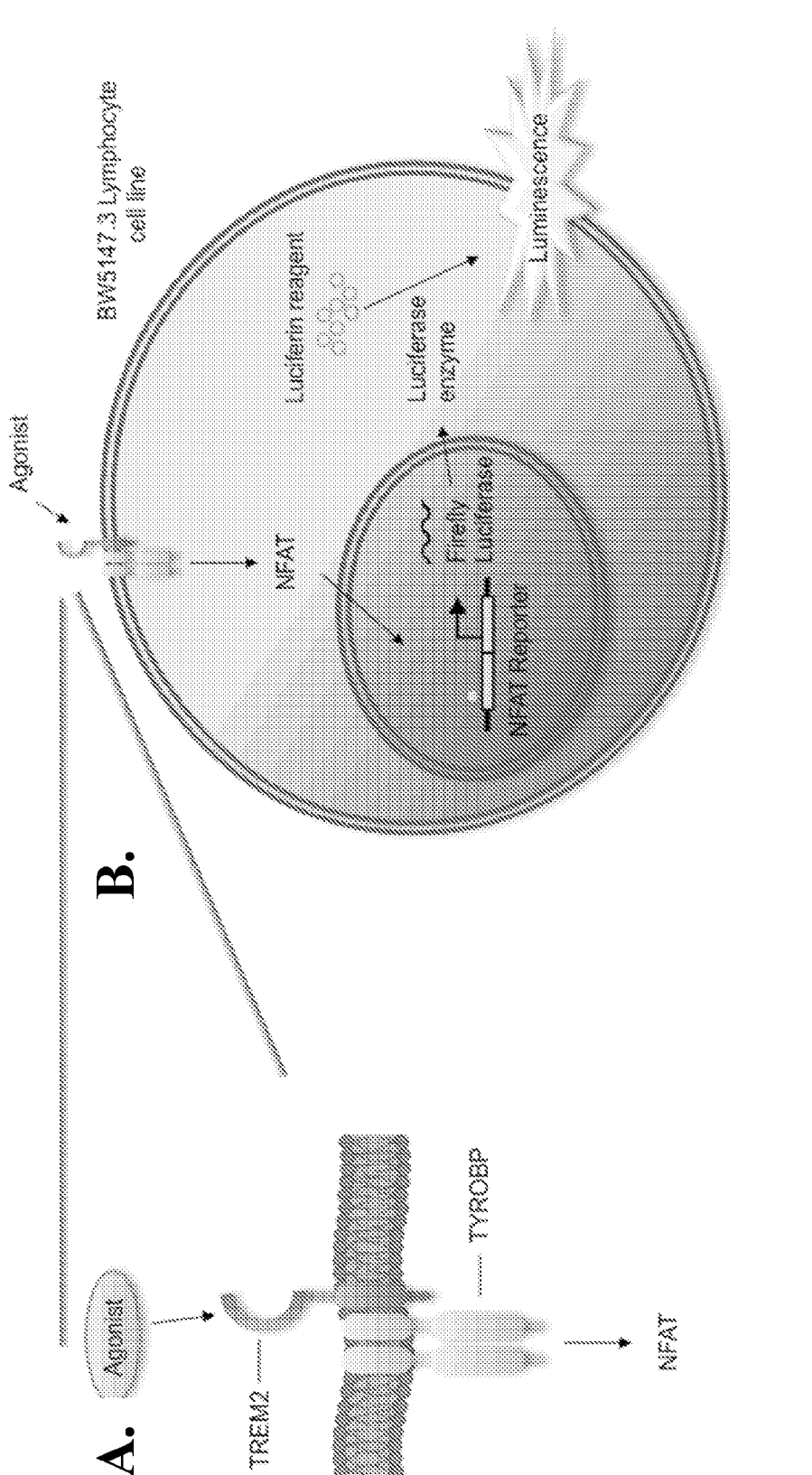
FIGS. 2A-2B depict an embodiment of the screening methods using a cell-based luciferase reporter.

Example 2. Establishing Luc Reporter Cell Lines for Identifying TREM2 Agonists Cell-based reporter assays were developed for identifying TREM2 agonists. A mouse T-lymphocyte cell line, BW5147.3, stably co-expressing full-length TREM2, full-length TYROBP, and a reporter (e.g., firefly luciferase) driven by NFAT-response elements, was established (FIG. 2). The parental BW5147.3 cells have no detectable expres-sion of TREM2 or TYROBP (FIG. 4B) and can be used as a counter screen cell-line to identify false positive com-pounds that stimulate reporter expression independent of TREM2 and TYROBP. BW5147.3 lymphocytes play a central role in the immune system and have high viability (99-100%) in culture.

Figures 4A, 4B, 4C, 4D:
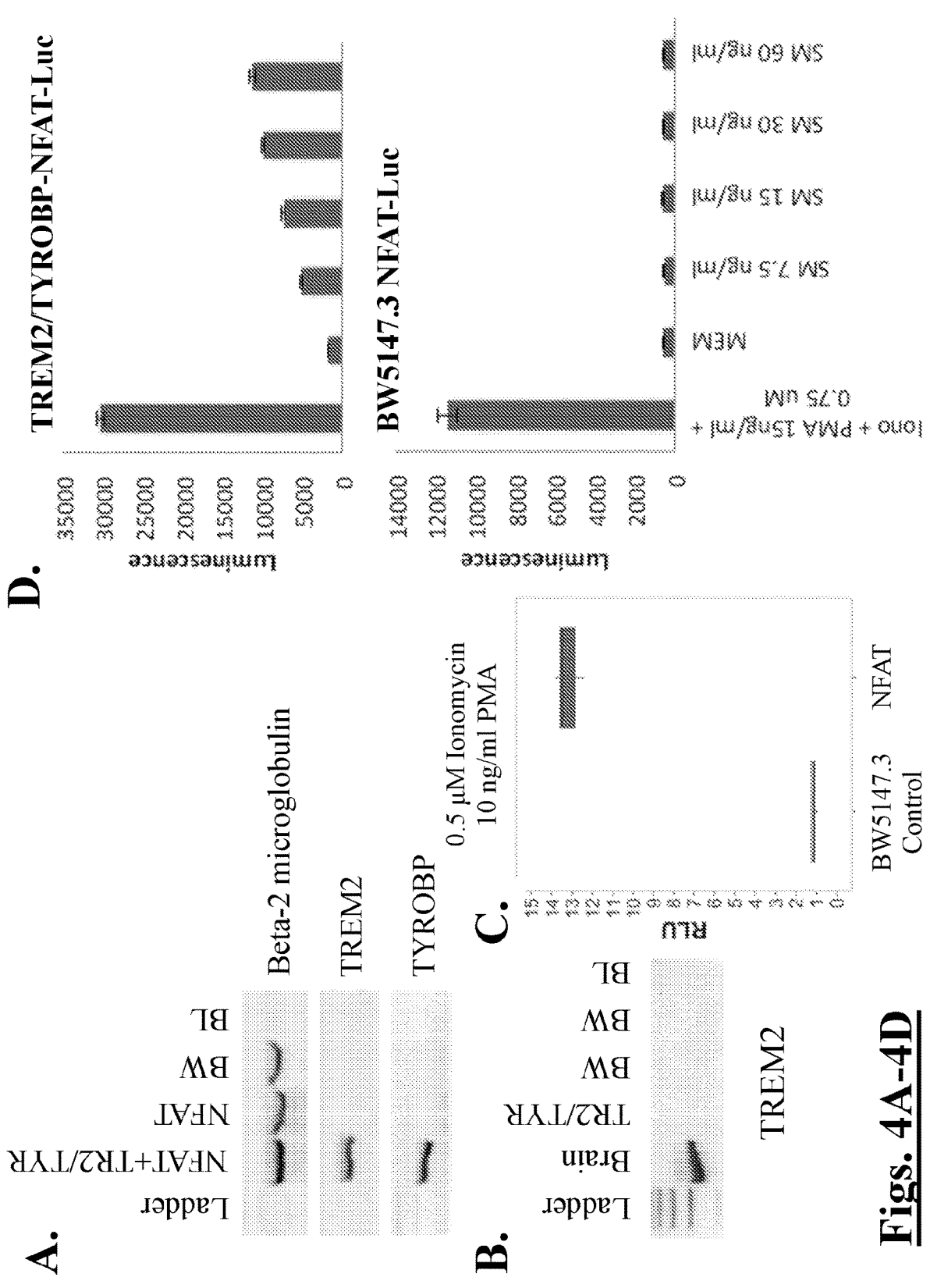
FIGS. 4A-4D depict TREM2/TYROBP mRNA expression and activity of the reporter cell lines.

TREM2 and TYROBP geneArt double-stranded cDNA strings were synthesized (Life Technologies, Carlsbad, CA) and subcloned into pTYF lentiviral vectors to generate a pLenti expression clone. HEK293HT cells were next trans-fected using Superfect (Qiagen, Venlo, Netherlands), and viral particles were collected and concentrated. Stable expression of TREM2, TYROBP, and the Cignal Lenti NFAT Reporter (Luc) (Qiagen, Venlo, Netherlands) in BW5147.3 cells was accomplished by transduction in opti-MEM media (Life Technologies, Carlsbad, CA) containing 6 μg/ml Polybrene (Sigma-Aldrich, St. Louis, MO). A triple antibiotic selection was used to select TREM2/TYROBP/NFAT-Luc positive clones, and RT-PCR and Western blot were used to verify stable expression of TYROBP and TREM2 (FIG. 4A).

Figure 3:
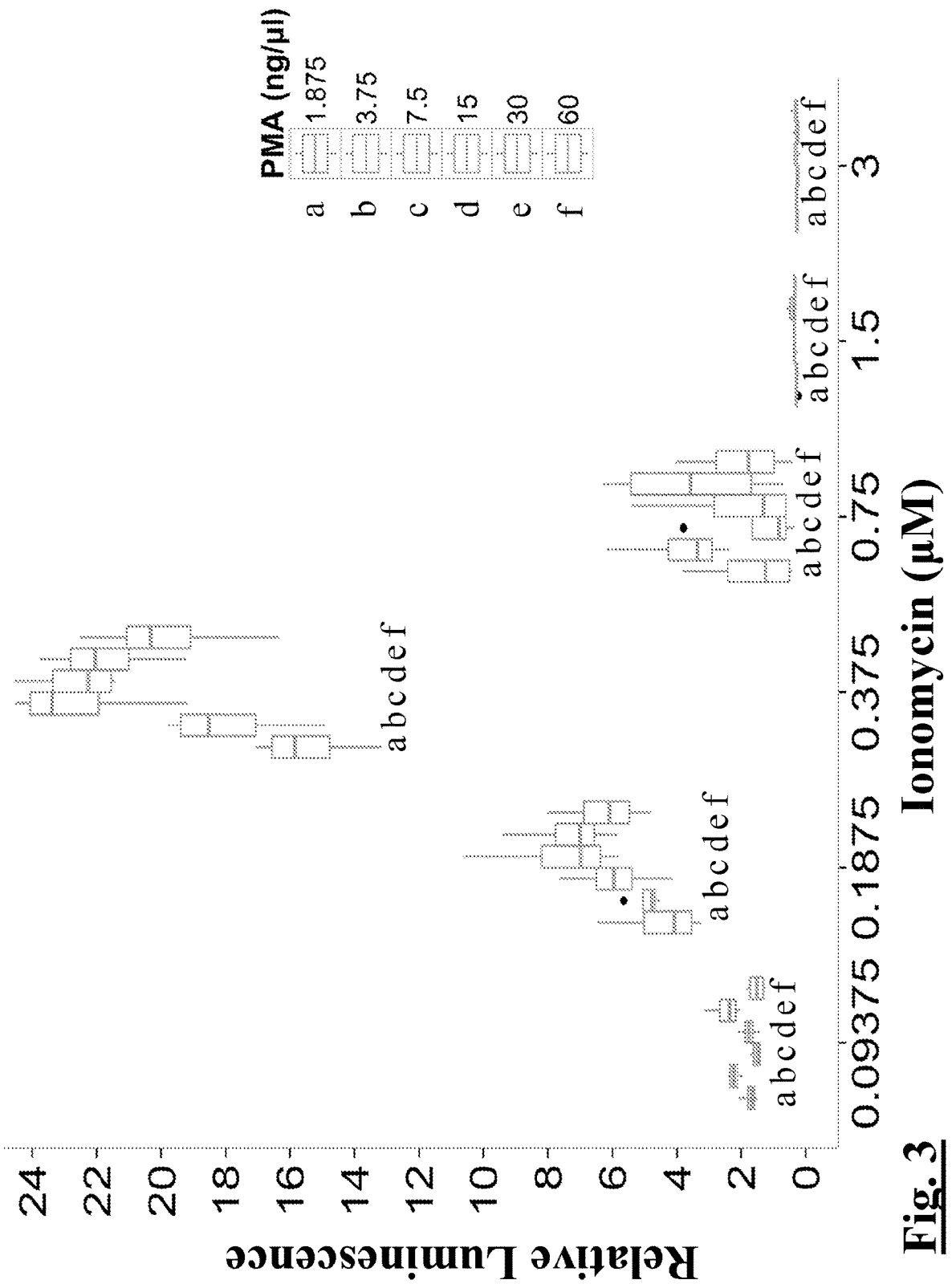
FIG. 3 depicts optimization of the assay using Phorbol 12-Myristate 13-Acetate (PMA) and ionomycin. PMA at 15 ng/μl and ionomycin at 0.375 μM produced a 22× signal to noise ratio.
Figure 5:
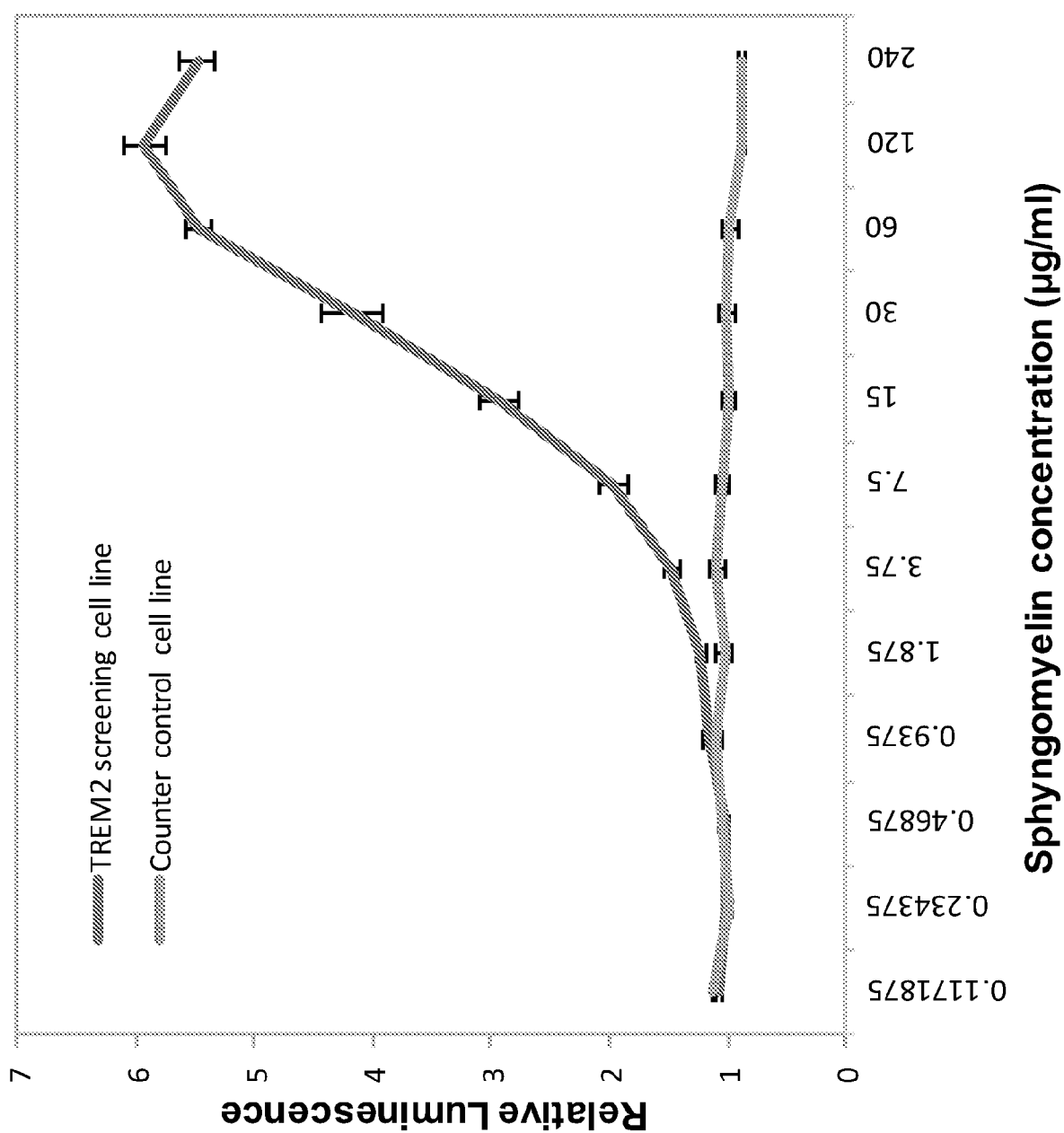
FIG. 5 depicts validation of the reporter cell line. Sphingomyelin stimulates TREM2/TYROBP/NFAT-Luc (NFAT+ TR2/TYR), the TREM2 screening cell line, but not the NFAT-Luc Reporter only (NFAT).

TREM2/TYROBP-NFAT-Luc cell line for HTS was opti-mized by testing TREM2-stimulated Luc-reporting as a function of growth medium, agonist concentration, induc-tion time, assay duration, and cell density. Reporter TREM2/TYROBP-NFAT-Luc cells and control counter screen cells (BW5147.3 NFAT-Luc) were seeded into a 384-well plate at densities of 1000-40,000 cells/well, and incubated at 37° C. for 2, 4, 8, 12, 20, or 24 hours. Firefly luciferase levels were measured by chemiluminescence (Bright-Glo™, Promega, WI). The medium condition was optimized by comparing full media with 5% FBS vs. Opti-MEM (reduced serum media) and MEM. Maximum signal-to-background and fold-induction of firefly luciferase were observed with MEM, at $5 \times 10^5$ cells/ml (or 25,000 cells/well) at 8 hours of cell incubation with 0.375 μM Ionomycin and 1-60 ng/ml Phorbol myristate acetate (PMA) (FIG. 3). Ionomycin and PMA together elicit synergistic stimulation of luciferase activity through NFAT (FIGS. 3 and 4C). The effect of reported TREM2 agonists to be served as positive controls were measured (FIG. 5), and the specific stimulation of our reporter through TREM2 by known ligand sphingomyelin was confirmed (FIG. 5). The results demonstrate that increasing concentrations of sphingomyelin (SM), a known ligand of TREM2, induce reporter activity in the reporter cell line. A counter screen cell line (NFTA-Luc) did not show any activity when SM was added, demonstrating Luciferase activity in the screening reporter is through the activation of TREM2.

A counter screen cell line only expressing the Cignal Lenti NFAT Reporter (luc) was also created in parallel to the reporter (BW-NFAT-Luc cell line). The BW-NFAT-Luc cell line has the same MOI as the TREM2/TYROBP-NFAT-Luc cell line (MOI=20) but without expression of TREM2 or TYROBP.

Transmembrane signaling via TREM2 is accomplished through an ITAM-bearing trans-membrane adaptor protein, TYROBP or DAP12. TREM2 activation leads to the induction of transcription factor NFAT. Activation of TREM2 by ligands leads to the phosphorylation of TYROBP, the activation of the reporter, and quantitative production of luciferase. Previous studies using TREM2/TYROBP/NFAT reporter cell-lines have confirmed the stimulation of NFAT transcription following TREM2 activation. Compounds that directly stimulate NFAT signaling (stimulate luciferase activity in the BW-NFAT-Luc cell line) are eliminated as false positive. Thus, the counter screen with BW-NFAT-Luc cell line eliminates the false positive hits and confirms hits from TREM2/TYROBP cell lines screened.

Example 3. Screening for Compounds that Activate TREM2

A pilot screen of 2,400 compounds was performed to identify agonists, followed by validation of positive hits by potency estimations (i.e., EC50) from drug dose-response curves and confirm TREM2 dependence by a BW-NF-NFAT-Luc counter screen. About half of the compounds were from the Prestwick Chemical Library® (PCL, Prestwick Chemical, Illrirck, France), which is a collection of 1,120 compounds that are all marketed off patent FDA-approved drugs. The PCL compounds were selected for their high chemical and pharmacological diversity, their known bioavailability, and their safety in humans. The collection has a significant ion-channel and CNS component. Notably, ~20% of the compounds are CNS drugs with well-annotated mechanisms of action. The other half of the screened compounds were from the 1,280-compound LOPAC library (Sigma-Aldrich, St. Louis, MO). This collection contains pharmacologically active compounds, and it also has a significant ion-channel and neurotransmission component.

The primary screening assay was conducted with a concentration of 5 µM for each of the 2,400 compounds (final 0.05% or 0.1% DMSO (v/v)) with two replicate screens with internal replicates. The TREM2/TYROBP-NFAT-Luc cell line was seeded in 384-well plates in MEM and incubated at 37° C. in a 5% $CO_2$ humidified atmosphere overnight, followed by compound treatment (together with positive control of PMA (1.5 ng/mL)/Ionomycin (375 nM), positive control of sphingomyelin (120 µg/mL), and negative vehicle control of DMSO) for 8 h. Subsequently, Luciferase activity was measured using Bright-Glo™ (Promega, Madison, WI). The Table shows the number of hits from the primary screen, which was defined as compounds that increase luciferase by 2-fold compared to the negative vehicle control (DMSO). As two of the compounds are in the LOPAC library and PCL, the screening resulted in 27 compounds that can be defined as initial hits.

TABLE

|  | LOPAC | Prestwick |
|---|---|---|
| Total compounds | 1280 | 1120 |
| >2× relative luminescence | 19 | 10 |
| >5× relative luminescence | 6 | 2 |

Figures 6A, 6B:
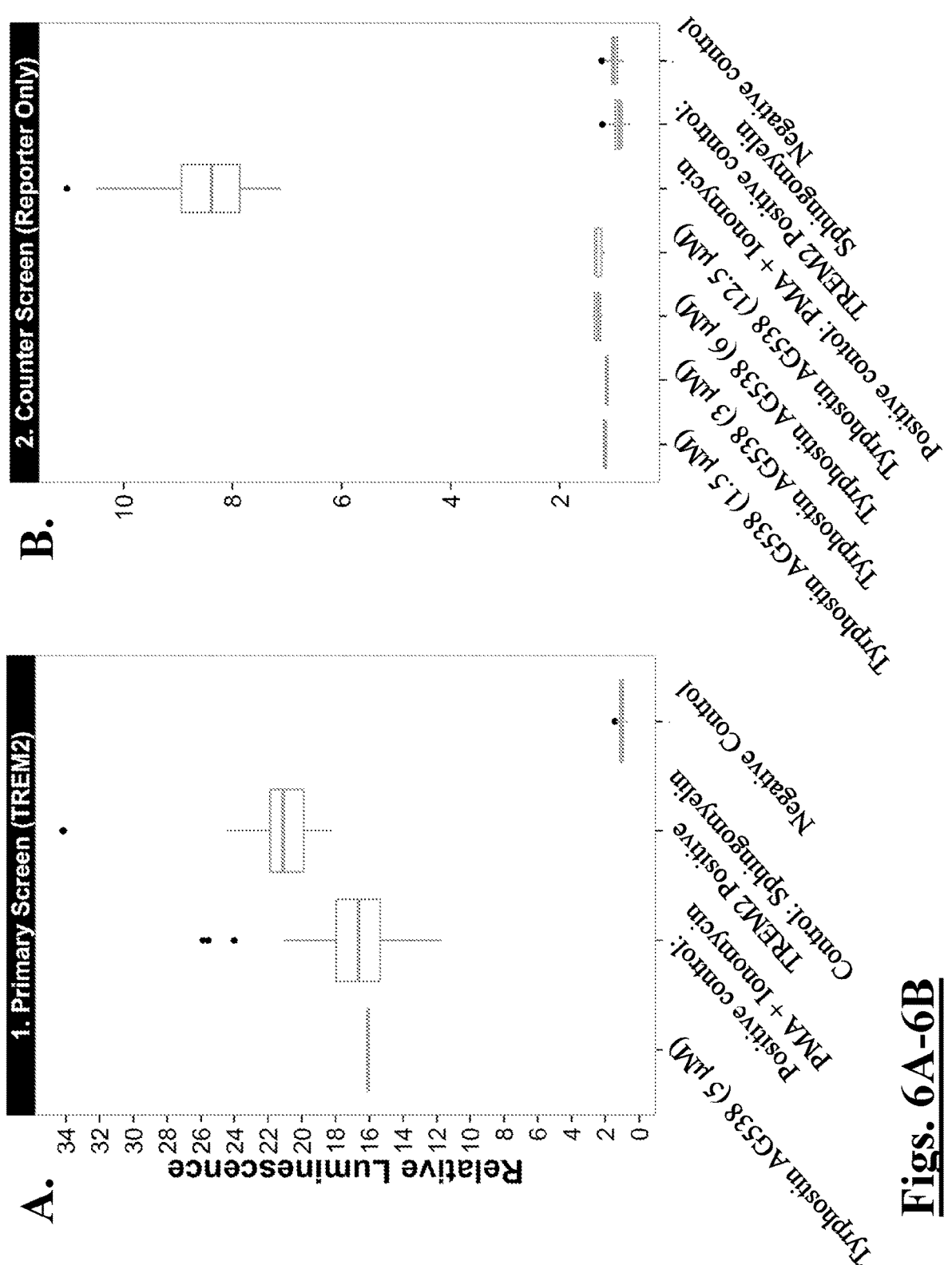
FIGS. 6A-6B depicts the results of compound screens.
Figure 7:
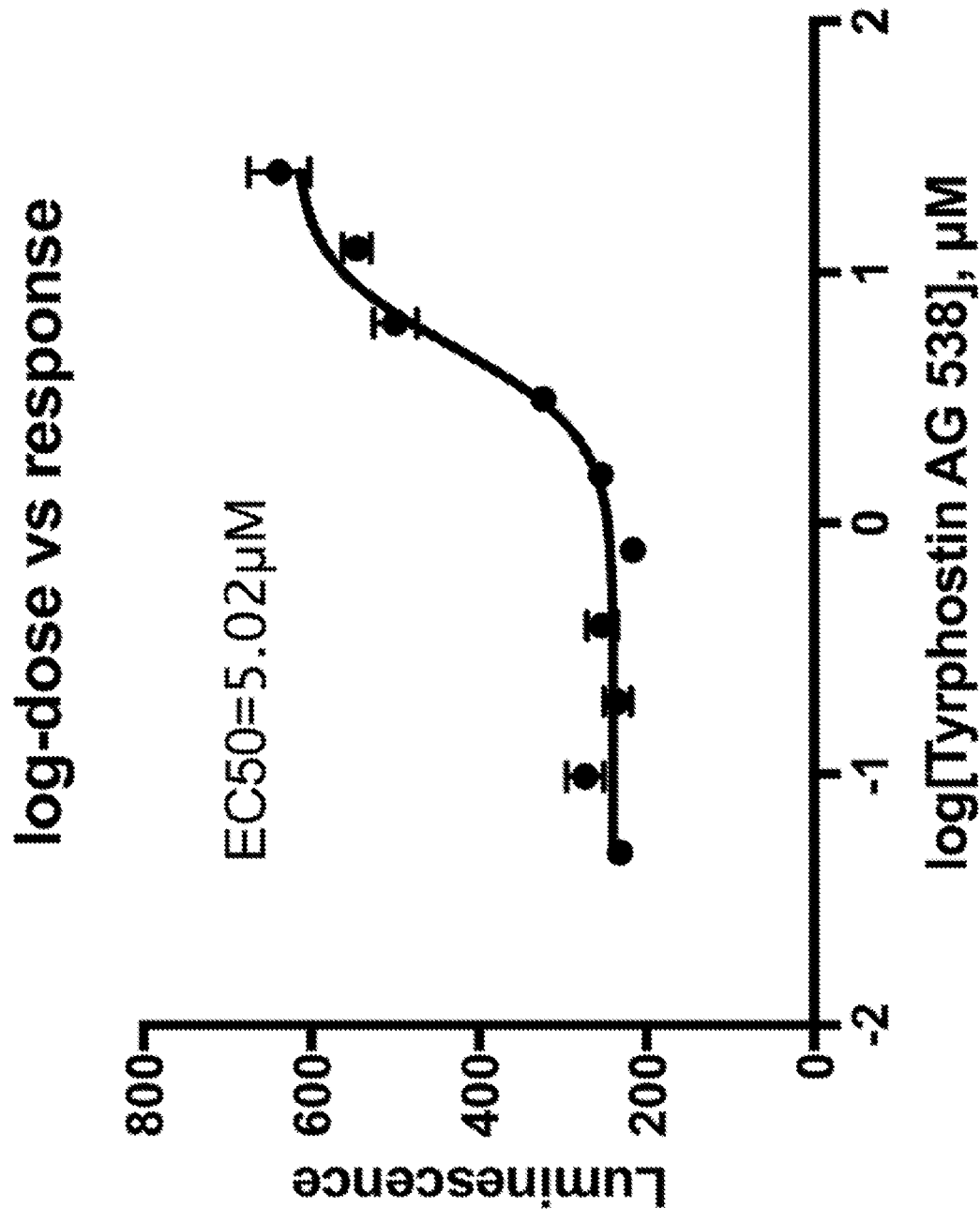
FIG. 7 depicts the dose-response curve and EC50 based on effects of a serial dilution of Tyrphostin AG 538 in the TREM2/TYROBP Luciferase reporter cell line.

To eliminate the false positive hits from the primary screen that might directly stimulate NFAT signaling, a counter screen was performed with the initial 27 compounds using the BW-NFAT-Luc cell line alone. The BW-NFAT-Luc cell line was seeded in 384-well plates in MEM and incubated at 37° C. in a 5% $CO_2$ humidified atmosphere overnight, followed by compound treatment in a 20-point serial dilution (100 µM to 0.4 nM) for each of the 27 compounds and with the positive control of PMA (1.5 ng/mL)/Ionomycin (375 nM), the positive control of sphingomyelin (120 µg/mL), and the negative vehicle control of DMSO. This revealed one compound, Tyrphostin AG 538, as a true positive hit. The primary screen with the TREM2/TYROBP Luciferase reporter cell line identified Tyrphostin AG 538 as a positive hit with a relative luminescence of 16.08 (FIG. 6A). Sphingomyelin (120 µg/mL), positive control and known TREM2 agonist, and PMA (1.5 ng/mL)/Ionomycin (375 nM), a positive control and known NFAT reporter stimulant, showed similarly positive results. FIG. 6B shows that various concentrations of Tyrphostin AG 538 (1.5-12.5 µM shown here) did not stimulate the NFAT reporter directly in the counter screen. Therefore, the activity of Tyrphostin AG 538 in the TREM2 primary screening cell line is due to the presence of TREM2/TYROBP. This suggests that Tyrphostin AG 538 is an agonist of the TREM2/TYROBP receptor signaling complex. In this experiment, PMA (1.5 ng·mL)/Ionomycin (375 nM), a known NFAT reporter stimulant, was used as a positive control. Sphingomyelin (120 µg/mL), a known TREM2 agonist did not show direct stimulation of the NFAT reporter either, as expected. FIG. 7 depicts the dose-response curve and EC50 calculations of a dilution series of Tyrphostin AG 538 in the TREM2/TYROBP Luciferase reporter cell line.

We claim:

1. A method of increasing phagocytosis of an apoptotic neuronal cell in a subject in need thereof, comprising administering to the subject Tyrphostin AG 538, or salts thereof, wherein the Tyrphostin AG 538, or salts thereof is administered in an amount sufficient to activate triggering receptor expressed on myeloid cells 2 (TREM2) in the subject.

2. The method of claim 1, wherein the subject is an animal model of a neurodegenerative disease or a human identified as having a neurodegenerative disease.

3. The method of claim 2 wherein the neurodegenerative disease is selected from the group consisting of: Alzheimer's disease (AD), Amyotrophic lateral sclerosis (ALS), Huntington's disease (HD), Parkinson's disease (PD), chronic traumatic encephalopathy, Dentatorubral-pallidoluysian atrophy (DRPLA), Spinocerebellar ataxia (SCA), Traumatic brain injury (TBI), Stroke, Paraneoplastic disorders, Systemic lupus erythematous, Multiple sclerosis (MS), and a Prion disease, and wherein the Prion disease is selected from the group consisting of: Creutzfeldt-Jakob disease (CJD), new variant CJD, Gerstmann-Sträussler-Scheinker syndrome (GSS), fatal familial insomnia (FFI), and kuru.

4. The method of claim 1, wherein the subject is an animal model of a disease associated with TREM2 or a human diagnosed with a disease associated with TREM2.

5. The method of claim 4, wherein the disease associated with TREM2 is selected from the group consisting of: a disease caused by a mutation in TREM2, a disease of which a TREM2 variant has been identified as a risk factor, a disease the outcome of which is affected by TREM2 deficiency, and a disease of which TREM2 is a potential therapeutical target.

6. The method of claim 5, wherein the disease associated with TREM2 is selected from the group consisting of: Nasu Hakola disease (NHD or PLOSL), frontotemporal dementia (FTD), Autoimmune Lymphoproliferative Syndrome (ALPS), Multiple sclerosis (MS), Amyotrophic lateral sclerosis (ALS), autoimmune encephalitis (AE), prion disease, stroke, pain, medial cerebral artery occlusion (MCAO), and traumatic brain injury (TBI).

7. The method of claim 1, wherein the apoptotic neuronal cell is a neuronal cell exhibiting an accumulation of a pathogenic protein, wherein the pathogenic protein is selected from the group consisting of: huntingtin with polyglutamine expansion, atrophin-1, ataxin-1, ataxin-2, ataxin-3, Aβ peptide (APP), hyperphosphorylated tau protein, α-Synuclein, Parkin, and Prion protein.

8. The method of claim 4, wherein the disease associated with TREM2 is a disease caused by a mutation in TREM2.

9. The method of claim 1, further comprising detecting an increase in activation of microglia in the subject after administering Tyrphostin AG 538.

\* \* \* \* \*